(12) United States Patent
Takahashi et al.

(10) Patent No.: US 6,899,886 B2
(45) Date of Patent: May 31, 2005

(54) ACYLACETONITRILES, PROCESS FOR PREPARATION THEREOF AND MITICIDES CONTAINING THE SAME

(75) Inventors: Nobuyoshi Takahashi, Naruto (JP); Satoshi Gotoda, Naruto (JP); Naoki Ishii, Naruto (JP); Yasuhiro Sasama, Naruto (JP)

(73) Assignee: Otsuka Chemical Co., Ltd., Osaka (JP)

( * ) Notice: Subject to any disclaimer, the term of this patent is extended or adjusted under 35 U.S.C. 154(b) by 265 days.

(21) Appl. No.: 10/343,811

(22) PCT Filed: Aug. 9, 2001

(86) PCT No.: PCT/JP01/06851
§ 371 (c)(1),
(2), (4) Date: Feb. 3, 2003

(87) PCT Pub. No.: WO02/14263
PCT Pub. Date: Feb. 21, 2002

(65) Prior Publication Data
US 2003/0208086 A1 Nov. 6, 2003

(30) Foreign Application Priority Data

Aug. 11, 2000 (JP) ........................................ 2000-244738
Dec. 14, 2000 (JP) ........................................ 2000-379844

(51) Int. Cl.[7] ........................ A01N 25/06; C07C 255/03
(52) U.S. Cl. ........................................ 424/405; 558/405
(58) Field of Search ........................ 558/405; 424/405

(56) References Cited

U.S. PATENT DOCUMENTS 4,031,243 A 6/1977 Aparicio et al.

FOREIGN PATENT DOCUMENTS

| EP | 1 201 646 A1 | 5/2002 |
|---|---|---|
| JP | 60-11452 A | 1/1985 |
| JP | 60-11401 A | 2/1985 |
| JP | 05-43518 A | 2/1993 |
| WO | WO 98/35935 A1 | 8/1998 |

OTHER PUBLICATIONS

K. Matsui, et al., "The Synthesis of 4–Chloro–3–benzoyl–2–azetinone Derivatives and Their Conversion into N–Benzoyl–2,4–azetidinedione Derivatives," Bulletin of the Chemical Society of Japan, (1973), vol. 46, No. 6, pp. 1755–1759.

Esther Dominguez, et al., "A Convenient One–Pot Preparative Method for 4,5–Diarylisoxazoles Involving Amine Exchange Reactions," J. Org. Chem., 1996 vol. 61, No. 16, pp. 5435–5439.

Alistair A. Finnie, et al., "The Synthesis of 1,5,7,10–Tetraoxygenated 3–Methylphenanthrenes," J. Chem. Research (S), 1987, pp. 78–79.

D. G. Buckley, et al., "The Synthesis and Degradation of 3–Acylphthalides," Aust, J. Chem., 1969, 22, pp. 577–595.

Michael Fedorynski, et al., "Sodium and Potassium Carbonates: Efficient Strong Bases in Solid–Liquid Two–Phase Systems," J. Org. Chem., vol. 43, No. 24, 1978, pp. 4682–4684.

E. S. Yim, et al., "Effects of ultrasound on the formation of α–benzoylbenzyl cyanide from benzyl cyanide and alkylphenyl ketone from α–alkylbenzyl cyanide by potassium superoxide in the presence of crown ether," Ultrasonics Sonochemistry 6 (1999) pp. 105–109.

*Primary Examiner*—Johann Richter
*Assistant Examiner*—Ebenezer Sackey
(74) *Attorney, Agent, or Firm*—Knobbe, Martens, Olson & Bear LLP

(57) ABSTRACT

The acylacetonitrile compound of the invention is represented by the formula (1):

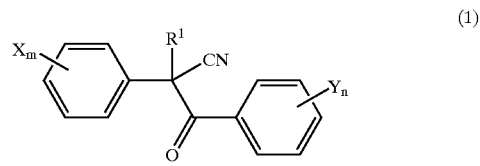

wherein $R^1$ represents $-C(O)ZR^2$; $R^2$ represents $C_{1-6}$ alkyl, $C_{1-4}$ haloalkyl or the like; Z represents oxygen or sulfur; X and Y independently represent halogen, $C_{1-6}$ alkyl or $C_{1-4}$ haloalkyl; and m and n are independently an integer of 1 to 3. The acylacetonitrile compound of the invention exhibits excellent miticidal and ovicidal activities for mites over a long period. Therefore, the acylacetonitrile compound of the invention is useful as a miticide.

19 Claims, No Drawings

ACYLACETONITRILES, PROCESS FOR PREPARATION THEREOF AND MITICIDES CONTAINING THE SAME

This application is the U.S. National Phase under 35 U.S.C. §371 of International Application PCT/JP01/06851, filed Aug. 9, 2001, which claims priority to Japanese Patent Application Nos. 2000-244738, filed Aug. 11, 2000, and 2000-379844, filed Dec. 14, 2000. The International Application was published under PCT Article 21(2) in a language other than English.

TECHNICAL FIELD

The present invention relates to a novel acylacetonitrile compound, a process for preparing the compound, and a miticide containing the compound.

BACKGROUND OF THE INVENTION

Japanese Unexamined Patent Publication No. 158137/1999 discloses a compound represented by the formula (A):

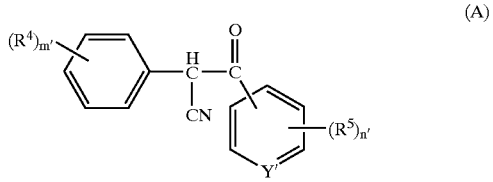

(A)

wherein $R^4$ and $R^5$ represent halogen, substituted or unsubstituted alkyl, or substituted or unsubstituted alkenyl; Y' represents $=C(R^6)-$ or $=N-$; $R^6$ represents hydrogen, halogen, alkyl or haloalkyl; m' is an integer of 0 to 5; and n' is an integer of 1 to 4. The compound represented by the formula (A) is a compound exhibiting keto-enol tautomerism as illustrated in the following formula.

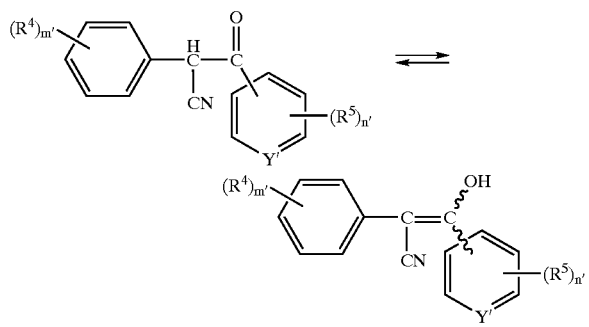

Said publication also discloses that the compounds represented by the formula (A) are useful as intermediates for preparing the acrylonitrile compounds represented by the formula (B):

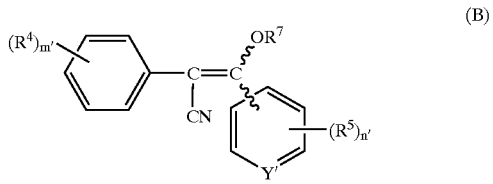

(B)

wherein $R^7$ represents alkyl, haloalkyl or the like; and $R^4$, $R^5$, m' and n' are as defined above.

Further, said publication discloses that the compounds represented by the formulas (A) and (B) exhibit miticidal activities.

However, said publication merely teaches in the examples that the compounds represented by the formula (A) exhibit miticidal and ovicidal activities for two-spotted spider mites when used at a high concentration of 800 ppm.

The present inventors have confirmed through experiments that the compounds represented by the formula (A) exhibit little miticidal and ovicidal activities for two-spotted spider mites when used at a low concentration.

In addition, although said publication discloses that the acrylonitrile compounds represented by the formula (B) are effective for mite control, the miticidal activities thereof are not satisfactory. Thus, in consideration of the life cycle of mites, the demand exists for a miticide that can control the damage caused by mites over a long period of about 14 to about 40 days depending on factors such as the kind of mite, the type of plants to which the miticide will be applied, etc. However, the acrylonitrile compounds represented by the formula (B) are not effective for controlling the damage caused by mites over a long period of about 14 to about 40 days.

Recently, some mites have developed resistance to the miticides that have been in use for many years, making it difficult to control them with conventional miticides. Thus, there are demands for the development of a novel miticide that can give excellent mite control.

DISCLOSURE OF THE INVENTION

It is an object of the present invention to provide an acylacetonitrile compound that demonstrates excellent mite control even when the compound is used at a low concentration.

It is another object of the invention to provide an acylacetonitrile compound that can maintain excellent mite control over a long period.

It is a further object of the invention to provide an acylacetonitrile compound that exhibits excellent mite control even for mites that have developed resistance to conventional miticides.

It is also an object of the invention to provide a process for preparing the acylacetonitrile compound described above.

It is still another object of the invention to provide a miticide containing the acylacetonitrile compound described above.

The present invention provides an acylacetonitrile compound represented by the formula (1):

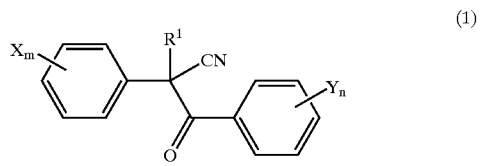

(1)

wherein $R^1$ represents $-C(O)ZR^2$; $R^2$ represents $C_{1-6}$ alkyl, $C_{1-4}$ haloalkyl, $C_{2-4}$ alkenyl, $C_{2-4}$ alkynyl, $C_{1-6}$ alkoxy-$C_{1-4}$ alkyl, $C_{1-4}$ alkylthio-$C_{1-4}$ alkyl or benzyl; Z represents oxygen or sulfur; X and Y independently represent halogen, $C_{1-6}$ alkyl or $C_{1-4}$ haloalkyl; m and n are independently an integer of 1 to 3; and m X's and n Y's may be the same or different, respectively.

The present invention provides a process for preparing the acylacetonitrile compound represented by the formula (1).

The process comprises reacting an α-substituted-phenylacetonitrile compound represented by the formula (2):

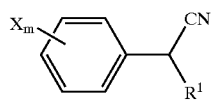

(2)

wherein R¹, X and m are as defined above, with a benzoyl halide represented by the formula (3):

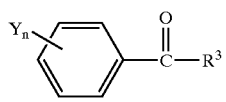

(3)

wherein Y and n are as defined above; and R³ represents halogen,
to obtain the acylacetonitrile compound represented by the formula (1):

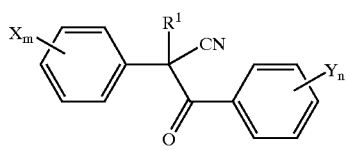

(1)

wherein R¹, X, m, Y and n are as defined above.

The present invention provides a miticide containing as an active ingredient the acylacetonitrile compound represented by the formula (1).

Acylacetonitrile Compound

In the present specification, the groups represented by each of R², X, Y, Z, and R³ can be exemplified as follows.

Examples of halogen atoms are fluorine, chlorine, bromine, iodine and the like.

Examples of $C_{1-6}$ alkyl groups include $C_{1-6}$ linear or branched alkyl groups such as methyl, ethyl, n-propyl, isopropyl, n-butyl, isobutyl, sec-butyl, tert-butyl, n-pentyl, isopentyl, neopentyl, n-hexyl, isohexyl and the like.

Examples of $C_{1-4}$ haloalkyl groups are $C_{1-4}$ linear or branched alkyl groups substituted with 1 to 9, preferably 1 to 5, halogen atoms and include fluoromethyl, chloromethyl, bromomethyl, iodomethyl, difluoromethyl, trifluoromethyl, 1-fluoroethyl, 2-fluoroethyl, 2-chloroethyl, 2,2,2-trifluoroethyl, pentafluoroethyl, 1-fluoropropyl, 2-chloropropyl, 3-fluoropropyl, 3-chloropropyl, 1-fluorobutyl, 1-chlorobutyl, 4-fluorobutyl and the like.

Examples of $C_{2-4}$ alkenyl groups include $C_{2-4}$ linear or branched alkenyl groups such as vinyl, 1-propenyl, allyl, isopropenyl, 1-butenyl, 2-butenyl, 3-butenyl, 1-methyl-2-propenyl, 1,3-butadienyl and the like.

Examples of $C_{2-4}$ alkynyl groups include $C_{2-4}$ linear or branched alkynyl groups such as ethynyl, 1-propynyl, 2-propynyl, 1-methyl-2-propynyl, 1-butynyl, 2-butynyl, 3-butynyl and the like.

Examples of $C_{1-6}$ alkoxy groups are $C_{1-6}$ linear or branched alkoxy groups and include methoxy, ethoxy, n-propoxy, isopropoxy, n-butoxy, isobutoxy, sec-butoxy, tert-butoxy, n-pentyloxy, isopentyloxy, neopentyloxy, n-hexyloxy, isohexyloxy and the like.

Examples of $C_{1-4}$ alkyl groups include $C_{1-4}$ linear or branched alkyl groups such as methyl, ethyl, n-propyl, isopropyl, n-butyl, isobutyl, sec-butyl and the like.

Examples of $C_{1-6}$ alkoxy-$C_{1-4}$ alkyl groups are $C_{1-4}$ linear or branched alkyl groups substituted with 1 to 4, preferably 1 to 2, $C_{1-6}$ linear or branched alkoxy groups and include methoxymethyl, ethoxymethyl, n-propoxymethyl, isopropoxymethyl, n-butoxymethyl, isobutoxymethyl, sec-butoxymethyl, tert-butoxymethyl, n-pentyloxymethyl, n-hexyloxymethyl, methoxyethyl, ethoxyethyl, n-propoxyethyl, isopropoxyethyl, n-butoxyethyl, isobutoxyethyl, sec-butoxyethyl, tert-butoxyethyl, 3-methoxypropyl, 3-ethoxypropyl, 3-ethoxybutyl and the like.

Examples of $C_{1-4}$ alkylthio groups include $C_{1-4}$ linear or branched alkylthio groups such as methylthio, ethylthio, n-propylthio, isopropylthio, n-butylthio, isobutylthio, sec-butylthio, tert-butylthio and the like.

Examples of $C_{1-4}$ alkylthio-$C_{1-4}$ alkyl groups are $C_{1-4}$ linear or branched alkyl groups substituted with 1 to 4, preferably 1 to 2, $C_{1-4}$ linear or branched alkylthio groups and include methylthiomethyl, methylthioethyl, ethylthiomethyl, ethylthioethyl, ethylthiopropyl, ethylthiobutyl, n-propylthiomethyl, isopropylthiomethyl, n-butylthioethyl and the like.

In acylacetonitrile compounds represented by the formula (1), Z is preferably oxygen.

In acylacetonitrile compounds represented by the formula (1), X is preferably halogen or $C_{1-6}$ alkyl.

In acylacetonitrile compounds represented by the formula (1), Y is preferably one species selected from halogens and $C_{1-4}$ haloalkyls.

Among the acylacetonitrile compounds represented by the formula (1), the preferred compounds are those wherein Z is oxygen, X is halogen or $C_{1-6}$ alkyl, and Y is halogen and/or $C_{1-4}$ haloalkyl.

Among the acylacetonitrile compounds represented by the formula (1), the more preferred compounds are those wherein Z is oxygen, X is $C_{1-6}$ alkyl, and Y is $C_{1-4}$ haloalkyl.

Moreover, preferred acylacetonitrile compounds are those wherein the halogen represented by X is chlorine, and the $C_{1-6}$ alkyl is isopropyl or tert-butyl; and those wherein m is 1. Most preferred compounds are those wherein the phenyl ring is substituted with X at 4-position.

Also preferred are those acylacetonitrile compounds wherein $C_{1-4}$ haloalkyl represented by Y is trihalogenomethyl, more preferably trifluoromethyl; and those acylacetonitrile compounds wherein n is 1. Most preferred compounds are those wherein the phenyl ring is substituted with Y at 2-position.

Method for Preparing Acylacetonitrile Compound

The acylacetonitrile compound of the present invention can be readily prepared according to following reaction scheme 1.

Reaction Scheme 1;

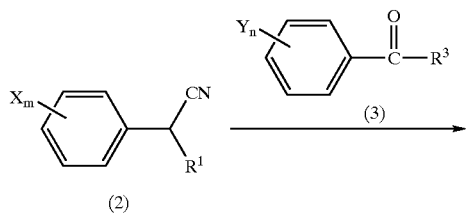

-continued

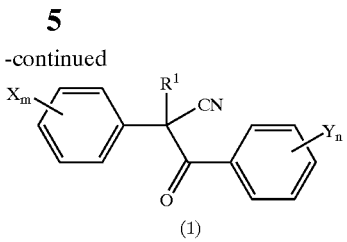

(1)

wherein R¹, X, Y, m, n, and R³ are as defined above.

As illustrated in the reaction scheme 1 above, the acylacetonitrile compound of the invention represented by the formula (1) is prepared by reacting the α-substituted-phenylacetonitrile compound represented by the formula (2) with the benzoyl halide represented by the formula (3).

The proportion of the α-substituted-phenylacetonitrile compound of the formula (2) to the benzoyl halide of the formula (3) used in the reaction is not limited and is suitably selected from a wide range. The latter is usually used in an amount of about 1 to about 5 moles, preferably about 1 mole, per mole of the former.

The above reaction can be carried out either in a suitable solvent or in the absence of solvent. Usable solvents for the reaction are not limited insofar as they are inert to the reaction. Examples of solvents are hexane, cyclohexane, heptane and like aliphatic or alicyclic hydrocarbons; benzene, chlorobenzene, toluene, xylene and like aromatic hydrocarbons; methylene chloride, 1,2-dichloroethane, chloroform, carbon tetrachloride and like halogenated hydrocarbons; diethyl ether, tetrahydrofuran, 1,4-dioxane and like ethers; methyl acetate, ethyl acetate and like esters; acetone, methylethylketone and like ketones; N,N-dimethylformamide and like amides; dimethylsulfoxide and like sulfoxides; etc.

These solvents can be used alone or in combination of two or more species as required.

The reaction temperature of the above reaction, although not limited, is usually in the range of −20° C. to the boiling point of the solvent used, preferably 0° C. to 25° C. The reaction time is usually in the range of about 0.5 to about 24 hours depending on factors such as the reaction temperature, etc.

The above reaction is preferably carried out in the presence of a base. A wide variety of known bases can be used. Examples are metallic sodium, metallic potassium and like alkali metals; sodium carbonate, potassium carbonate, sodium bicarbonate and like alkali metal carbonates; sodium hydroxide, potassium hydroxide and like alkali metal hydroxides; sodium hydride, potassium hydride and like alkali metal hydrides; sodium methoxide, sodium ethoxide, potassium tert-butoxide and like alkali metal alkoxides; and triethylamine, pyridine and like organic bases.

These bases can be used alone or in combination of two or more species.

The amount of the base is equivalent or more, preferably about 1 to about 5 equivalents, relative to the α-substituted-phenylacetonitrile compound of the formula (2).

When an organic base such as triethylamine, pyridine or the like is used, it can be used in large excess to serve also as a reaction solvent.

The α-substituted-phenylacetonitrile compounds represented by the formula (2) used as starting compound in reaction scheme 1 include novel compounds as well as known compounds, and are prepared according to, for example, the following reaction scheme 2.

Reaction Scheme 2;

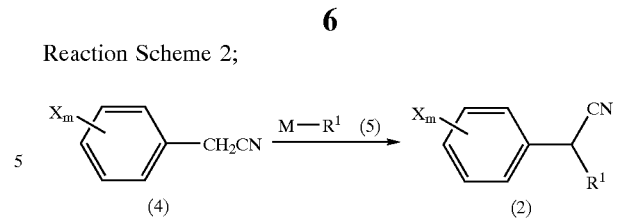

wherein R¹, X and m are as defined above; M represents halogen or —ZR²; and R² and Z are as defined above.

As illustrated in the reaction scheme 2 above, the α-substituted-phenylacetonitrile compound represented by the formula (2) is prepared in a simple manner by reacting the phenylacetonitrile represented by the formula (4) with the compound represented by the formula (5).

The proportion of the phenylacetonitrile represented by the formula (4) to the compound represented by the formula (5) used in the reaction is not limited and is suitably selected from a wide range. The latter is usually used in an amount of about 1 to about 10 moles, preferably about 1 mole, per mole of the former.

The above reaction can be carried out in a suitable solvent or in the absence of solvent. Usable solvents for the reaction are not limited insofar as they are inert to the reaction. Examples of solvents are hexane, cyclohexane, heptane and like aliphatic or alicyclic hydrocarbons; benzene, chlorobenzene, toluene, xylene and like aromatic hydrocarbons; methylene chloride, 1,2-dichloroethane, chloroform, carbon tetrachloride and like halogenated hydrocarbons; diethyl ether, tetrahydrofuran, 1,4-dioxane and like ethers; methyl acetate, ethyl acetate and like esters; acetone, methylethylketone and like ketones; N,N-dimethylformamide and like amides; dimethylsulfoxide and like sulfoxides; etc.

These solvents can be used alone or in combination of two or more species as required.

The reaction temperature of the above reaction, although not limited, is in the range of −20° C. to the boiling point of the solvent used, preferably 0° C. to 25° C. Usually, the reaction is completed in about 0.5 to about 24 hours depending on factors such as the reaction temperature, etc.

The above reaction is preferably carried out in the presence of a base. A wide variety of known bases can be used. Examples are metallic sodium, metallic potassium and like alkali metals; sodium carbonate, potassium carbonate, sodium bicarbonate and like alkali metal carbonates; sodium hydroxide, potassium hydroxide and like alkali metal hydroxides; sodium hydride, potassium hydride and like alkali metal hydrides; sodium methoxide, sodium ethoxide, potassium tert-butoxide and like alkali metal alkoxides; and triethylamine, pyridine and like organic bases.

These bases can be used alone or in combination of two or more species.

The amount of base is usually equivalent or more, preferably about 1 to about 5 equivalents, relative to the phenylacetonitrile of the formula (4).

An organic base such as triethylamine, pyridine or the like can be used in large excess to serve also as a reaction solvent.

Among the α-substituted-phenylacetonitrile compounds represented by the formula (2) as prepared above, those α-substituted-phenylacetonitrile compounds represented by the following formula (2a) and having a tert-butyl substituent at 4-position of the phenyl ring are novel compounds, which are not described in the literature:

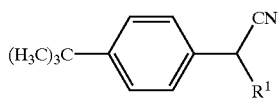

(2a)

wherein R¹ is as defined above.

The benzoyl halides represented by the formula (3) and used as starting compound in reaction scheme 1 are either known compounds or compounds that can be easily prepared according to the known methods described in, for example, Org. Synth., IV, 715 (1963), etc.

The phenylacetonitriles represented by the formula (4) and the compounds represented by the formula (5) used as starting compounds in reaction scheme 2 are, respectively, either known compounds or the compounds that can be easily prepared according to the known methods described in, for example, Org. Synth., I, 107 (1941), Ann., 35 283. (1840), etc.

The acylacetonitrile compounds represented by the formula (1) prepared according to the method illustrated in reaction scheme 1 and the α-substituted-phenylacetonitriles represented by the formula (2) prepared according to the method illustrated in reaction scheme 2 can be easily isolated from the respective reaction mixtures and purified by a known isolating and purifying procedure such as filtration, solvent extraction, distillation, recrystallization, column chromatography, etc.

Miticide

The compound of the present invention can be used as a miticide by itself. However, it is preferable to use in combination with a solid carrier, liquid carrier or gaseous carrier (propellant), and optionally with a surfactant and other adjuvants added thereto; it is formulated into various forms such as oil solutions, emulsifiable concentrates, wettable powders, flowables, granules, dusts, aerosols, fumigants or the like according to known preparation methods.

The acylacetonitrile compound of the invention is generally contained in these formulations in a proportion of 0.01 to 95 wt. %, preferably 0.1 to 50 wt. %.

Examples of solid carriers usable for a component in the formulations include those solid carriers used in known miticides such as clays, inorganic minerals, chemical fertilizers, etc. Specific examples of clays are kaolin clay, diatomaceous earth, water-containing synthetic precipitated silica, bentonite, fubasami clay, acid clay and the like. Specific examples of inorganic minerals are talc, ceramic, celite, quartz, sulfur, active carbon, calcium carbonate, hydrated silica and the like. Specific examples of chemical fertilizers are ammonium sulfate, ammonium phosphate, ammonium nitrate, urea, ammonium chloride and the like. These solid carriers are used in a fine, powdery or granular form.

Examples of liquid carriers usable for the preparation of formulations include those known liquid carriers used in miticides such as water, alcohols, ketones, aromatic hydrocarbons, aliphatic hydrocarbons, esters, nitrites, ethers, acid amides, halogenated hydrocarbons, dimethyl sulfoxide, vegetable oils, etc. Specific examples of alcohols are methanol, ethanol and the like. Specific examples of ketones are acetone, methylethylketone and the like. Specific examples of aromatic hydrocarbons are benzene, toluene, xylene, ethylbenzene, methylnaphthalene and the like. Specific examples of aliphatic hydrocarbons are hexane, cyclohexane, kerosene, light oil and the like. Specific examples of esters are ethyl acetate, butyl acetate and the like. Specific examples of nitrites are acetonitrile, isobutyronitrile and the like. Specific examples of ethers are diisopropyl ether, dioxane and the like. Specific examples of acid amides are N,N-dimethylformamide, N,N-dimethylacetamide and the like. Specific examples of halogenated hydrocarbons are dichloromethane, trichloroethane, carbon tetrachloride and the like. Specific examples of vegetable oils are soybean oil, cottonseed oil and the like.

Examples of gaseous carriers usable for the preparation of formulations include those known gaseous carriers used in miticides such as butane gas, LPG (liquefied petroleum gas), dimethyl ether, carbon dioxide gas and the like.

As a surfactant, known surfactants can be widely used. Examples include alkyl sulfates, alkylsulfonates, alkylarylsulfonates, alkyl aryl ethers and polyoxyethylene adducts thereof, polyethylene glycol ethers, polyhydric alcohol esters, sugar alcohol compounds and the like.

Examples of adjuvants include fixing agents, dispersants, stabilizers, etc.

Examples of the fixing agents and dispersants include casein, gelatin, polysaccharides, lignin derivatives, bentonite, sugars, water-soluble synthetic polymers and the like. Specific examples of polysaccharides include starch, gum arabic, cellulose derivatives, alginic acid and the like. Specific examples of synthetic water-soluble polymers include polyvinyl alcohol, polyvinyl pyrrolidone, polyacrylic acids and the like.

Stabilizers to be used include a wide range of known stabilizers usually used in this field. Examples are PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils (e.g., epoxidized linseed oil, etc.), mineral oils, fatty acids or esters thereof, etc.

The miticide of the invention can be used as it is or as diluted, for example, with water. The miticide can also be used in a mixture with other insecticides, nematocides, acaricides, fungicides, herbicides, plant growth control agents, synergists, soil conditioners, animal feeds and the like; and can be simultaneously used with such agents without mixing.

As a miticide for agricultural use, the compound of the invention is usually applied in an amount of 0.1 to 500 g, preferably 1 to 100 g, per 1,000 m of the area. When the compound of the invention is used in the form of emulsifiable concentrates, wettable powders, flowables or the like and diluted with water, the compound is usually applied in a concentration of 1 to 1,000 ppm, preferably 10 to 500 ppm. When the miticide of the invention is used in the form of granules, powders or the like, it can be applied as such without dilution.

The amount or concentration of application, although exemplified above, can be suitably increased or decreased according to the type of formulation, time of application, place of application, method of application, kind of insect, severity of damage, etc.

The mites against which the miticide of the invention is effective are plant parasites, for example, two-spotted spider mites, carmine spider mites, citrus red mites, Kanzawa spider mites, fruit tree red spider mites (European red mites), broad mites, pink citrus rust mites, bulb mites and the like.

EFFECT OF THE INVENTION

The acylacetonitrile compounds of the invention represented by the formula (1) are effective, even at a low dose, against harmful mites and the like.

The acylacetonitrile compounds of the invention exhibit excellent mite control against various mites even when used at a low concentration. The term "mite control" employed herein means miticidal activities effective at every stage of the life cycle of mites (e.g., egg, larva and imago).

The acylacetonitrile compounds of the invention exhibit excellent mite control over an extended period of 14 to 40 days.

The acylacetonitrile compounds of the invention show excellent mite control even for those mites having developed resistance to conventional miticides.

The acylacetonitrile compounds of the invention are satisfactory with regard to safety in that they do not affect plants; honeybee, *Trichogramma evanescens, Encarsia formosa*, minute pirate bug (Orius spp.) and like beneficial insects; *Phytoseiulus persimilis* and like beneficial predacious mites; etc.

BEST MODE FOR CARRYING OUT THE INVENTION

The present invention is described in more detail with reference to the following preparation examples, formulation examples and test examples, but the scope of the present invention is not limited by these examples.

PREPARATION EXAMPLE 1

Preparation of Methyl 2-(4-Tert-Butylphenyl)Cyanoacetate (Compound No. (2)-1)

0.66 g (16.5 mmols) of sodium hydride and 2.6 g (15.0 mmols) of 4-tert-butylphenylacetonitrile were suspended in 50 ml of tetrahydrofuran. To the suspension was added dropwise 1.95 g (16.5 mmols) of dimethyl carbonate dissolved in 10 ml of tetrahydrofuran while stirring at room temperature. The mixture was refluxed with heating for 2 hours, and the solvent was distilled off under reduced pressure. Water was added to the residue, and the residue was acidified by diluted hydrochloric acid and twice extracted with 30 ml of ethyl acetate. The ethyl acetate extraction solutions were mixed, washed with a saturated brine solution, and dried over anhydrous magnesium sulfate. The solvent was distilled off under reduced pressure. The residue thus-obtained was purified by silica gel column chromatography (n-hexane:ethyl acetate=2:1), giving 1.8 g of the desired product (yield 52%)

α-Substituted-phenylacetonitrile compounds represented by the formula (2) were prepared in the same manner as described in preparation example 1 except that the 4-tert-butyl phenylacetonitrile was replaced with corresponding phenylacetonitriles.

Table 1 shows the compounds thus obtained and their properties, and table 2 shows the $^1$H-NMR data of the compounds.

TABLE 1

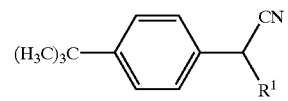

| Compound No. (2)-No. | R$^1$ | Property |
|---|---|---|
| 1 | —CO$_2$CH$_3$ | Viscous oil |
| 2 | —CO$_2$CH$_2$CH$_3$ | Viscous oil |
| 3 | —CO$_2$CH(CH$_3$)$_2$ | Viscous oil |
| 4 | —CO$_2$C(CH$_3$)$_3$ | Viscous oil |
| 5 | —CO$_2$CH$_2$(CH$_2$)$_4$CH$_3$ | Viscous oil |
| 6 | —CO$_2$CH$_2$C$_6$H$_5$ | Viscous oil |
| 7 | —CO$_2$CH$_2$CH=CH$_2$ | Viscous oil |
| 8 | —CO$_2$CH$_2$C≡CH | Viscous oil |
| 9 | —CO$_2$CH$_2$CF$_3$ | Viscous oil |
| 10 | —CO$_2$CH$_2$CH$_2$OCH$_3$ | Viscous oil |
| 11 | —CO$_2$CH$_2$CH$_2$OC$_2$H$_5$ | Viscous oil |
| 12 | —CO$_2$CH$_2$CH$_2$OCH$_2$CH$_2$CH$_3$ | Viscous oil |
| 13 | —CO$_2$CH$_2$CH$_2$OCH(CH$_3$)$_2$ | Viscous oil |
| 14 | —CO$_2$CH$_2$CH$_2$OCH$_2$(CH$_2$)$_2$CH$_3$ | Viscous oil |
| 15 | —CO$_2$CH$_2$CH$_2$OC(CH$_3$)$_3$ | Viscous oil |
| 16 | —CO$_2$CH$_2$CH$_2$SCH$_3$ | Viscous oil |
| 17 | —C(O)SCH$_3$ | Viscous oil |
| 18 | —C(O)SC$_2$H$_5$ | Viscous oil |
| 19 | —C(O)SCH$_2$CH$_2$CH$_3$ | Viscous oil |
| 20 | —C(O)SCH(CH$_3$)$_2$ | Viscous oil |
| 21 | —C(O)SCH$_2$(CH$_2$)$_2$CH$_3$ | Viscous oil |
| 22 | —C(O)SCH$_2$(CH$_2$)$_4$CH$_3$ | Viscous oil |

TABLE 2

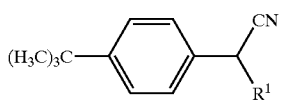

| Compound No. (2)-No. | $^1$H-NMR (CDCl$_3$, ppm) |
|---|---|
| 1 | 1.32(s, 9H), 3.81(s, 3H), 4.71(s, 1H), 7.41(dd, 4H) |
| 2 | 1.2–1.4(m, 12H), 4.25(q, 2H), 4.69(s, 1H), 7.41(dd, 4H) |
| 3 | 1.2–1.4(m, 15H), 4.65(s, 1H), 5.0–5.1(m, 1H), 7.40(dd, 4H) |
| 4 | 1.32(s, 9H), 1.46(s, 9H), 4.58(s, 1H), 7.35(d, 2H), 7.40(d, 2H) |
| 5 | 0.8–0.9(m, 3H), 1.2–1.4(m, 15H), 1.6–1.7(m, 2H), 4.18(t, 2H), 4.69(s, 1H), 7.40(dd, 4H) |
| 6 | 1.32(s, 9H), 4.73(s, 1H), 5.20(s, 2H), 7.2–7.5(m, 9H) |

TABLE 2-continued

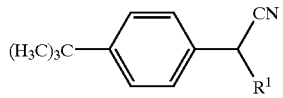

| Compound No. (2)-No. | ¹H-NMR (CDCl₃, ppm) |
|---|---|
| 7 | 1.31(s, 9H), 4.67(dm, 2H), 4.73(s, 1H), 5.26(dd, 1H), 5.31(dd, 1H), 5.8–6.0 (m, 1H), 7.38(d, 2H), 7.44(d, 2H) |
| 8 | 1.32(s, 9H), 2.52(t, 1H), 4.75(s, 1H), 4.76(dd, 2H), 7.38(d, 2H), 7.44(d, 2H) |
| 9 | 1.32(s, 9H), 4.5–4.6(m, 2H), 4.81(s, 1H), 7.38(d, 2H), 7.45(d, 2H) |
| 10 | 1.32(s, 9H), 3.09(s, 3H), 3.6–3.65(m, 2H), 4.3–4.35(m, 2H), 4.75(s, 1H), 7.40(d, 2H), 7.41(d, 2H) |
| 11 | 1.32(s, 9H), 1.15(t, 3H), 3.45(q, 2H), 3.7–3.75(m, 2H), 4.3–4.35(m, 2H), 4.74(s, 1H), 7.38(d, 2H), 7.40(d, 2H) |
| 12 | 0.88(t, 3H), 1.33(s, 9H), 1.5–1.6(m, 2H), 3.36(t, 2H), 3.6–3.36(m, 2H), 4.3–4.35(m, 2H), 4.74(s, 1H), 7.38(d, 2H), 7.43(d, 2H) |
| 13 | 1.08(d, 3H), 1.10(d, 3H), 1.31(s, 9H), 3.5–3.6(m, 1H), 3.6–3.65(m, 2H), 4.3–4.35(m, 2H), 4.74(s, 1H), 7.41(s, 4H) |
| 14 | 0.91(t, 3H), 1.32(s, 9H), 1.3–1.4(m, 2H), 1.5–1.6(m, 2H), 3.40(t, 2H), 3.6–3.65(m, 2H), 4.3–4.35(m, 2H), 4.74(s, 1H), 7.38(d, 2H), 7.43(d, 2H) |
| 15 | 1.12(s, 9H), 1.31(s, 9H), 3.5–3.55(m, 2H), 4.3–4.35(m, 2H), 4.73(s, 1H), 7.41(s, 4H) |
| 16 | 1.32(s, 9H), 2.11(s, 3H), 2.73(t, 2H), 4.35(t, 2H), 4.73(s, 1H), 7.38(d, 2H), 7.44(d, 2H) |
| 17 | 1.32(s, 9H), 2.44(s, 3H), 4.79(s, 1H), 7.46(d, 2H), 7.50(d, 2H) |
| 18 | 1.26(t, 3H), 1.32(s, 9H), 2.91(q, 2H), 4.77(s, 1H), 7.38(d, 2H), 7.44(d, 2H) |
| 19 | 0.95(t, 3H), 1.32(s, 9H), 1.5–1.7(m, 2H), 2.90(dt, 2H), 4.78(s, 1H), 7.37(d, 2H), 7.43(d, 2H) |
| 20 | 1.3–1.4(m, 15H), 3.6–3.7(m, 1H), 4.73(s, 1H), 7.35(d, 2H), 7.43(d, 2H) |
| 21 | 0.89(t, 3H), 1.3–1.4(m, 2H), 1.33(s, 9H), 1.5–1.6(m, 2H), 2.91(t, 2H), 4.77(s, 1H), 7.36(d, 2H), 7.43(d, 2H) |
| 22 | 0.85(t, 3H), 1.32(s, 9H), 1.2–1.4(m, 6H), 1.5–1.6(m, 2H), 2.91(t, 2H), 4.77(s, 1H), 7.36(d, 2H), 7.43(d, 2H) |

PREPARATION EXAMPLE 2
Preparation of Methyl 2-(4-Chlorophenyl)-2-(2-Trifluoromethylbenzoyl)Cyanoacetate (Compound No. 30)

0.10 g (2.6 mmols) of sodium hydride was suspended in 20 ml of tetrahydrofuran. To the suspension was added dropwise, while stirring and cooling, 5 ml of a tetrahydrofuran solution in which 0.42 g (2.0 mmols) of methyl 2-(4-chlorophenyl)cyanoacetate and 0.41 g (2.6 mmols) of 2-trifluoromethylbenzoyl chloride had been dissolved. The mixture was stirred at room temperature over night. The reaction mixture was poured into ice water. The water phase thereof was acidified by diluted hydrochloric acid and twice extracted with 30 ml of ethyl acetate. The ethyl acetate extraction solutions were mixed, washed with a saturated brine solution, and dried over anhydrous magnesium sulfate. The solvent was distilled off under reduced pressure. The residue thus-obtained was purified by silica gel column chromatography (n-hexane:benzene=1:1), giving 0.45 g of the desired product (yield 59%).

Acylacetonitrile compounds represented by the formula (1) of the invention were prepared in the same manner as described in preparation example 2 except that the methyl 2-(4-chlorophenyl)cyanoacetate was replaced with corresponding α-substituted-phenylacetonitrile compounds, and/or the 2-trifluoromethylbenzoyl chloride was replaced with corresponding benzoyl chlorides.

Table 3 shows the compounds thus obtained and their properties, and table 4 shows the ¹H-NMR data of the compounds.

TABLE 3

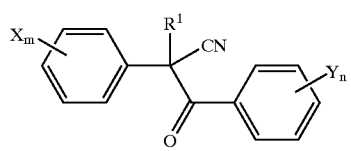

| Compound No. | Xm | Yn | R¹ | Melting point(° C.) |
|---|---|---|---|---|
| 1 | 4-C(CH₃)₃ | 2-CF₃ | —CO₂CH₃ | 137–139 |
| 2 | 4-C(CH₃)₃ | 2-CF₃ | —CO₂C₂H₅ | 141–142 |
| 3 | 4-C(CH₃)₃ | 2-CF₃ | —CO₂CH(CH₃)₂ | 141–142 |
| 4 | 4-C(CH₃)₃ | 2-CF₃ | —CO₂C(CH₃)₃ | 137–138 |
| 5 | 4-C(CH₃)₃ | 2-CF₃ | —CO₂CH₂(CH₂)₄CH₃ | 83–84 |

TABLE 3-continued

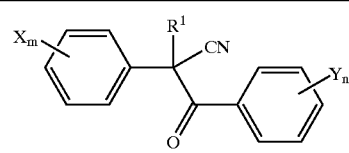

| Compound No. | Xm | Yn | R¹ | Melting point(° C.) |
|---|---|---|---|---|
| 6 | 4-C(CH$_3$)$_3$ | 2-CF$_3$ | —CO$_2$CH$_2$C$_6$H$_5$ | Viscous oil |
| 7 | 4-C(CH$_3$)$_3$ | 2-CF$_3$ | —CO$_2$CH$_2$CH═CH$_2$ | 107–108 |
| 8 | 4-C(CH$_3$)$_3$ | 2-CF$_3$ | —CO$_2$CH$_2$C≡CH | 106–108 |
| 9 | 4-C(CH$_3$)$_3$ | 2-CF$_3$ | —CO$_2$CH$_2$CF$_3$ | 94–95 |
| 10 | 4-C(CH$_3$)$_3$ | 2-CF$_3$ | —CO$_2$CH$_2$CH$_2$OCH$_3$ | 73–74 |
| 11 | 4-C(CH$_3$)$_3$ | 2-CF$_3$ | —CO$_2$CH$_2$CH$_2$OC$_2$H$_5$ | Viscous oil |
| 12 | 4-C(CH$_3$)$_3$ | 2-CF$_3$ | —CO$_2$CH$_2$CH$_2$OCH$_2$CH$_2$CH$_3$ | Viscous oil |
| 13 | 4-C(CH$_3$)$_3$ | 2-CF$_3$ | —CO$_2$CH$_2$CH$_2$OCH(CH$_3$)$_2$ | Viscous oil |
| 14 | 4-C(CH$_3$)$_3$ | 2-CF$_3$ | —CO$_2$CH$_2$CH$_2$OCH$_2$(CH$_2$)$_2$CH$_3$ | Viscous oil |
| 15 | 4-C(CH$_3$)$_3$ | 2-CF$_3$ | —CO$_2$CH$_2$CH$_2$OC(CH$_3$)$_3$ | Viscous oil |
| 16 | 4-C(CH$_3$)$_3$ | 2-CF$_3$ | —CO$_2$CH$_2$CH$_2$SCH$_3$ | Viscous oil |
| 17 | 4-C(CH$_3$)$_3$ | 2-CF$_3$ | —C(O)SCH$_3$ | 113–116 |
| 18 | 4-C(CH$_3$)$_3$ | 2-CF$_3$ | —C(O)SC$_2$H$_5$ | 113–114 |
| 19 | 4-C(CH$_3$)$_3$ | 2-CF$_3$ | —C(O)SCH$_2$CH$_2$CH$_3$ | 85–87 |
| 20 | 4-C(CH$_3$)$_3$ | 2-CF$_3$ | —C(O)SCH(CH$_3$)$_2$ | 81–84 |
| 21 | 4-C(CH$_3$)$_3$ | 2-CF$_3$ | —C(O)SCH$_2$(CH$_2$)$_2$CH$_3$ | Viscous oil |
| 22 | 4-C(CH$_3$)$_3$ | 2-CF$_3$ | —C(O)SCH$_2$(CH$_2$)$_4$CH$_3$ | Viscous oil |
| 23 | 2-Cl | 2-CF$_3$ | —CO$_2$C$_2$H$_5$ | 71–73 |
| 24 | 3-Cl | 2-CF$_3$ | —CO$_2$C$_2$H$_5$ | 89–92 |
| 25 | 4-Cl | 2-CF$_3$ | —CO$_2$C$_2$H$_5$ | Viscous oil |
| 26 | 2,4-Cl$_2$ | 2-CF$_3$ | —CO$_2$C$_2$H$_5$ | 70–72 |
| 27 | 2,6-Cl$_2$ | 2-CF$_3$ | —CO$_2$C$_2$H$_5$ | 132–134 |
| 28 | 3,4-Cl$_2$ | 2-CF$_3$ | —CO$_2$C$_2$H$_5$ | 66–68 |
| 29 | 3,5-Cl$_2$ | 2-CF$_3$ | —CO$_2$C$_2$H$_5$ | 123–124 |
| 30 | 4-Cl | 2-CF$_3$ | —CO$_2$CH$_3$ | 89–92 |
| 31 | 4-Cl | 2-CF$_3$ | —CO$_2$CH$_2$CH$_2$CH$_3$ | 60–62 |
| 32 | 4-Cl | 2-CF$_3$ | —CO$_2$CH(CH$_3$)$_2$ | Viscous oil |
| 33 | 4-Cl | 2-CF$_3$ | —CO$_2$CH$_2$(CH$_2$)$_2$CH$_3$ | 42–43 |
| 34 | 4-Cl | 2-CF$_3$ | —CO$_2$C(CH$_2$)$_3$ | 94–97 |
| 35 | 4-Cl | 2-CF$_3$ | —CO$_2$CH$_2$CH(CH$_3$)$_2$ | 94–96 |
| 36 | 4-C(CH$_3$)$_3$ | 2-CF$_3$, 4-F | —CO$_2$C$_2$H$_5$ | 111–112 |
| 37 | 4-C(CH$_3$)$_3$ | 2-CF$_3$, 5-F | —CO$_2$C$_2$H$_5$ | 110–112 |
| 38 | 4-C(CH$_3$)$_3$ | 2-CF$_3$, 6-F | —CO$_2$C$_2$H$_5$ | Viscous oil |
| 39 | 4-Cl | 2-Cl | —CO$_2$C$_2$H$_5$ | Viscous oil |
| 40 | 4-Cl | 2-F | —CO$_2$CH$_3$ | 59–60 |
| 41 | 4-Cl | 2-Br | —CO$_2$CH$_3$ | Viscous oil |
| 42 | 4-Cl | 2-CH$_3$ | —CO$_2$CH$_3$ | 65–68 |
| 43 | 4-Cl | 2,6-F$_2$ | —CO$_2$CH$_3$ | Viscous oil |
| 44 | 4-F | 2-CF$_3$ | —CO$_2$C$_2$H$_5$ | 75–76 |
| 45 | 4-Br | 2-CF$_3$ | —CO$_2$C$_2$H$_5$ | 43–45 |
| 46 | 4-CH$_3$ | 2-CF$_3$ | —CO$_2$C$_2$H$_5$ | 57–58 |
| 47 | 4-CF$_3$ | 2-CF$_3$ | —CO$_2$C$_2$H$_5$ | Viscous oil |
| 48 | 4-CH(CH$_3$)$_2$ | 2-CF$_3$ | —CO$_2$C$_2$H$_5$ | 79–80 |
| 49 | 4-CH$_2$CH(CH$_3$)$_2$ | 2-CF$_3$ | —CO$_2$C$_2$H$_5$ | 38–40 |

TABLE 4

| Compound No. | ¹H-NMR (CDCl$_3$, ppm) |
|---|---|
| 1 | 1.35(s, 9H), 3.92(s, 3H), 7.07(d, 1H), 7.4–7.7(m, 6H), 7.78(d, 1H) |
| 2 | 1.34(t, 3H), 1.35(s, 9H), 4.2–4.5(m, 2H), 7.07(d, 1H), 7.4–7.5(m, 3H), 7.5–7.6(m, 3H), 7.78(d, 1H) |
| 3 | 1.2–1.4(m, 15H), 5.1–5.2(m, 1H), 7.08(d, 1H), 7.4–7.6(m, 6H), 7.79(d, 1H) |
| 4 | 1.35(s, 9H), 1.52(s, 9H), 7.05(d, 1H), 7.4–7.6(m, 6H), 7.77(d, 1H) |
| 5 | 0.8–1.0(m, 3H), 1.2–1.4(m, 15H), 1.6–1.8(m, 2H), 4.2–4.4(m, 2H), 7.07(d, 1H), 7.4–7.6(m, 6H), 7.78(d, 1H) |

TABLE 4-continued

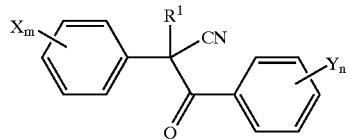

| Compound No. | $^1$H-NMR (CDCl$_3$, ppm) |
|---|---|
| 6 | 1.34(s, 9H), 5.3–5.4(m, 2H), 7.04(d, 1H), 7.3–7.6(m, 11H), 7.75(d, 1H) |
| 7 | 1.35(s, 9H), 4.7–4.9(m, 2H), 5.30(dd, 1H), 5.38(dd, 1H), 5.9–6.0(m, 1H), 7.07(d, 1H), 7.4–7.7 (m, 6H), 7.78(d, 1H) |
| 8 | 1.34(s 9H), 2.55(t, 1H), 4.87(d, 2H), 7.10(d, 1H), 7.4–7.6(m, 6H), 7.77(d, 1H) |
| 9 | 1.36(s, 9H), 4.6–4.8(m, 2H), 6.98(d, 1H), 7.4–7.7(m, 6H), 7.80(d, 1H) |
| 10 | 1.35(s, 9H), 3.36(s, 3H), 3.6–3.65(m, 2H), 4.4–4.5(m, 2H), 7.14(d, 1H), 7.4–7.6(m, 6H), 7.78(d, 1H) |
| 11 | 1.17(t, 3H), 1.34(s, 9H), 3.50(q, 2H), 3.6–3.7(m, 2H), 4.4–4.5(m, 2H), 7.15(d, 1H), 7.4–7.6(m, 6H), 7.80(d, 1H) |
| 12 | 0.89(t, 3H), 1.34(s, 9H), 1.5–1.6(m, 2H), 3.40(t, 2H), 3.65–3.7(m, 2H), 4.4–4.5(m, 2H), 7.15(d, 1H), 7.4–7.6(m, 6H), 7.79(d, 1H) |
| 13 | 1.1–1.2(m, 6H), 1.34(s, 9H), 3.5–3.6(m, 1H), 3.6–3.65(m, 2H), 4.3–4.35(m, 2H), 7.14(d, 1H), 7.4–7.6(m, 6H), 7.77(d, 1H) |
| 14 | 0.90(t, 3H), 1.34(s, 9H), 1.3–1.4(m, 2H), 1.5–1.6(m, 2H), 3.44(t, 2H), 3.6–3.7(m, 2H), 4.4–4.5 (m, 2H), 7.15(d, 1H), 7.4–7.6(m, 6H), 7.77(d, 1H) |
| 15 | 1.16(s, 9H), 1.34(s, 9H), 3.6–3.65(m, 2H), 4.4–4.45(m, 2H), 7.17(d, 1H), 7.4–7.6(m, 6H), 7.76(d, 1H) |
| 16 | 1.35(s, 9H), 2.14(s, 3H), 2.77(t, 2H), 4.4–4.6(m, 2H), 7.08(d, 1H), 7.4–7.6(m, 6H), 7.77(d, 1H) |
| 17 | 1.35(t, 3H), 2.42(s, 3H), 7.19(d, 1H), 7.5–7.65(m, 6H), 7.77(d, 1H) |
| 18 | 1.29(t, 3H), 1.35(s, 9H), 2.99(qd, 2H), 7.21(d, 1H), 7.4–7.6(m, 6H), 7.76(d, 1H) |
| 19 | 0.97(t, 3H), 1.35(s, 9H), 1.5–1.7(m, 2H), 2.8–3.1(m, 2H), 7.22(d, 1H), 7.4–7.7(m, 6H), 7.76(d, 1H) |
| 20 | 1.2–1.4(m, 15H), 3.6–3.8(m, 1H), 7.23(d, 1H), 7.4–7.7(m, 6H), 7.76(d, 1H) |
| 21 | 0.91(t, 3H), 1.3–1.4(m, 2H), 1.35(s, 9H), 1.5–1.6(m, 2H), 2.9–3.1(m, 2H), 7.22(d, 1H), 7.4–7.6 (m, 6H), 7.76(d, 1H) |
| 22 | 0.87(t, 3H), 1.2–1.4(m, 6H), 1.35(s, 9H), 1.5–1.7(m, 2H), 2.9–3.1(m, 2H), 7.22(d, 1H), 7.4–7.6 (m, 6H), 7.76(d, 1H) |
| 23 | 1.28(t, 3H), 4.15(q, 2H), 7.3–7.4(m, 2H), 7.4–7.5(m, 2H), 7.7–7.9(m, 3H), 8.2–8.3(m, 1H) |
| 24 | 1.34(t, 3H), 4.3–4.5(m, 2H), 7.14(d, 1H), 7.4–7.7(m, 6H), 7.80(d, 1H) |
| 25 | 1.34(t, 3H), 4.3–4.5(m, 2H), 7.12(d, 1H), 7.4–7.8(m, 6H), 7.79(d, 1H) |
| 26 | 1.30(t, 3H), 4.18(q, 2H), 7.30(dd, 1H), 7.40(d, 1H), 7.49(d, 1H), 7.7–7.8(m, 2H), 7.8–7.9(m, 1H), 8.2–8.3(m, 1H) |
| 27 | 1.28(t, 3H), 4.19(q, 2H), 7.28(d, 1H), 7.39(s, 1H), 7.42(d, 1H), 7.7–7.8(m, 2H), 7.8–7.9 (m, 1H), 8.2–8.3(m, 1H) |
| 28 | 1.34(t, 3H), 4.3–4.5(m, 2H), 7.19(d, 1H), 7.5–7.9(m, 6H) |
| 29 | 1.35(t, 3H), 4.3–4.5(m, 2H), 7.21(d, 1H), 7.50(d, 1H), 7.5–7.7(m, 4H), 7.81(d, 1H) |
| 30 | 3.93(s, 3H), 7.12(d, 1H), 7.4–7.5(m, 3H), 7.6–7.7(m, 3H), 7.80(d, 1H) |
| 31 | 0.96(t, 3H), 1.6–1.8(m, 2H), 4.2–4.4(m, 2H), 7.11(d, 1H), 7.4–7.5(m, 3H), 7.6–7.7(m, 3H), 7.79(d, 1H) |
| 32 | 1.28(d, 3H), 1.34(d, 3H), 5.1–5.2(m, 2H), 7.13(d, 1H), 7.4–7.5(m, 3H), 7.6–7.7(m, 3H), 7.89(d, 1H) |
| 33 | 0.93(t, 3H), 1.3–1.5(m, 2H), 1.6–1.8(m, 2H), 4.2–4.4(m, 2H), 7.10(d, 1H), 7.4–7.6(m, 3H), 7.6–7.7(m, 3H), 7.62(d, 1H) |
| 34 | 1.51(s, 9H), 7.13(d, 1H), 7.3–7.7(m, 6H), 7.79(d, 1H) |
| 35 | 0.95(d, 6H), 1.9–2.1(m, 1H), 4.0–4.2(m, 2H), 7.10(d, 1H), 7.4–7.5(m, 3H), 7.6–7.7(m, 3H), 7.62(d, 1H) |
| 36 | 1.3–1.4(m, 12H), 4.2–4.5(m, 2H), 7.1–7.2(m, 2H), 7.4–7.6(m, 5H) |
| 37 | 1.3–1.4(m, 12H), 4.2–4.5(m, 2H), 6.65(m, 1H), 7.2–7.3(m, 1H), 7.4–7.6(m, 4H), 7.7–7.8 (m, 1H) |
| 38 | 1.3–1.4(m, 12H), 4.2–4.5(m, 2H), 7.3–7.4(m, 1H), 7.45(d, 1H), 7.5–7.7(m, 4H) |
| 39 | 1.33(t, 3H), 4.2–4.5(m, 2H), 7.1–7.2(m, 2H), 7.3–7.4(m, 4H), 7.5–7.6(m, 2H) |
| 40 | 3.91(s, 3H), 7.20(dd, 1H), 7.2–7.5(m, 5H), 7.6–7.7(m, 3H), 7.8–7.9(m, 1H) |
| 41 | 3.93(s, 3H), 7.17(d, 1H), 7.3–7.4(m, 2H), 7.4–7.5(m, 2H), 7.6–7.7(m, 3H) |
| 42 | 2.48(s, 3H), 3.91(s, 3H), 7.10(t, 1H), 7.3–7.5(m, 6H), 7.56(dd, 1H) |
| 43 | 3.93(s, 3H), 6.9–7.1(m, 2H), 7.4–7.6(m, 5H) |
| 44 | 1.34(t, 3H), 4.3–4.5(m, 2H), 7.10(d, 1H), 7.1–7.2(m, 2H), 7.50(t, 1H), 7.6–7.8(m, 3H), 7.79(d, 1H) |
| 45 | 1.34(t, 3H), 4.3–4.5(m, 2H), 7.12(d, 1H), 7.5–7.7(m, 6H), 7.79(d, 1H) |
| 46 | 1.34(t, 3H), 2.41(s, 3H), 4.3–4.5(m, 2H), 7.04(d, 1H), 7.2–7.3(m, 2H), 7.45(t, 1H), 7.5–7.6(m, 3H), 7.77(d, 1H) |
| 47 | 1.34(t, 3H), 4.3–4.5(m, 2H), 7.17(d, 1H), 7.53(t, 1H), 7.6–7.8(m, 6H) |
| 48 | 1.28(d, 6H), 1.34(t, 3H), 2.9–3.1(m, 1H), 4.2–4.5(m, 2H), 7.06(d, 1H), 7.34(d, 2H), 7.46 (t, 1H), 7.5–7.7(m, 3H), 7.78(d, 1H) |
| 49 | 0.91(d, 6H), 1.34(t, 3H), 1.8–2.0(m, 1H), 2.52(d, 2H), 4.3–4.5(m, 2H), 7.02(d, 1H), 7.26 (d, 2H), 7.43(t, 1H), 7.5–7.6 (m, 3H), 7.77(d, 1H) |

Given below are formulation examples in which the parts refers to parts by weight.

FORMULATION EXAMPLE 1 (EMULSIFIABLE CONCENTRATE)

10 parts of each compound of the invention was dissolved in 45 parts of Solvesso 150 and 35 parts of N-methylpyrrolidone. 10 parts of emulsifier (trade name: Sorpol 3005X, manufactured by Toho kagaku Co., Ltd.) was added thereto. These ingredients were mixed while stirring, thereby producing a 10% emulsifiable concentrate.

FORMULATION EXAMPLE 2 (WETTABLE POWDER)

20 parts of each compound of the invention was added to the mixture of 2 parts of sodium lauryl sulfate, 4 parts of sodium lignin sulfonate, 20 parts of fine powders of water-containing synthetic silicon oxide and 54 parts of clay. These ingredients were mixed while stirring by a juice mixer, thereby producing 20% wettable powders.

FORMULATION EXAMPLE 3 (GRANULE)

5 parts of each compound of the invention was mixed with 2 parts of sodium dodecylbenzenesulfonate, 10 parts of bentonite and 83 parts of clay, followed by thorough agitation. A suitable amount of water was added, and the mixture was further stirred. The mixture was granulated by a granulator and air-dried, producing 5% granules.

FORMULATION EXAMPLE 4 (DUST)

1 part of each compound of the invention was dissolved in a suitable amount of acetone. To the solution were added 5 parts of fine powders of water-containing synthetic silicon oxide, 0.3 parts of acidic isopropyl phosphate (PAP) and 93.7 parts of clay, followed by mixing and stirring by a juice mixer. Acetone was removed therefrom by evaporation, producing a 1% powder formulation.

FORMULATION EXAMPLE 5 (FLOWABLE PREPARATION)

20 parts of each compound of the invention was mixed with 20 parts of water containing 3 parts of polyoxyethylene tristyrylphenyl ether phosphoric acid ester triethanolamine and 0.2 parts of Rhodorsil 426R (manufactured by Rhodia Chimie). The mixture was pulverized by a mill (trade name: DYNO-Mill, manufactured by Willy A. Bachofen AG) using a wet method, and further mixed with 60 parts of water containing 8 parts of propylene glycol and 0.32 parts of xanthane gum, thereby producing a 20% suspension in water.

Test examples are given below to demonstrate that the compound of the invention is useful as an active ingredient of a miticide.

TEST EXAMPLE 1 (MITICIDAL TEST ON TWO-SPOTTED SPIDER MITES)

A piece of non-woven fabric (4.5×5.5 cm) was suspended inside a plastic cup through an incision made in the lid of the plastic cup. After water was poured into the cup, the cup was covered with the lid. A kidney bean leaf (about 3.5×4.5 cm) was then placed on the sufficiently soaked, non-woven fabric. Another kidney bean leaf with two-spotted spider mites (about 30 mite samples) was placed on top of the first leaf, and the fabric and leaves were placed in a thermostatic chamber having a temperature of 25±2° C. and a humidity of 40%.

Miticidal formulations containing the compound of the invention (200 ppm) were prepared by adding an aqueous solution (100 ppm) of Sorpol 355 (manufactured by Toho Kagaku Co., Ltd.) to a methanol solution of the compound of the invention.

These miticidal formulations were sprayed onto the leaves, and the leaves were air-dried and placed in a thermostatic chamber (25±2° C., humidity 50%). The mortality rate of the two-spotted spider mites was calculated after 2 days.

The compounds that exhibited the mortality rate of 50% or more are as follows:
Compound Nos. 1, 2, 3, 4, 5, 6, 7, 8, 9, 10, 11, 12, 13, 14, 15, 16, 17, 18, 19, 20, 21, 22, 25, 30, 31, 32, 33, 35, 36, 38, 44, 45, 47, 48 and 49.

TEST EXAMPLE 2 (OVICIDAL TEST ON TWO-SPOTTED SPIDER MITES)

A piece of non-woven fabric (4.5×5.5 cm) was suspended inside a plastic cup through an incision made in the lid of the plastic cup. After water was poured into the cup, the cup was covered with the lid. A kidney bean leaf (about 3.5×4.5 cm) was then placed on the sufficiently soaked, non-woven fabric. Twenty female adults of two-spotted spider mite were placed on top of the leaf, and the fabric and leaf were placed in a thermostatic chamber having a temperature of 25±2° C., a humidity of 40% and 16L8D.

The next day, after the number of the female adults was adjusted once more to 20, 2 ml of a miticidal formulation containing the compound of the invention (200 ppm) prepared in the same manner as in test example 1 was sprayed onto the leaf, and the leaf was air-dried and placed in a thermostatic chamber (25±2° C., humidity 50%). The ovicidal rate of the two-spotted spider mites was calculated 6 days after the spraying of the miticidal formulation.

The compounds that exhibited the mortality rate of 50% or more are as follows:
Compound Nos. 1, 2, 3, 4, 5, 6, 7, 8, 9, 10, 11, 12, 13, 14, 15, 16, 17, 18, 19, 20, 21, 22, 25, 30, 31, 32, 33, 35, 36, 38, 44, 45, 48 and 49.

TEST EXAMPLE 3 (MITICIDAL TEST ON TWO-SPOTTED SPIDER MITES)

(1) As Test Compounds, The Following Compounds Were Used:
Test compound A: Compound No. 1 in table 3 (the compound of the invention).
Test compound B: Compound No. 2 in table 3 (the compound of the invention).
Test compound C: Compound No. 10 in table 3 (the compound of the invention).
Test compound D: Intermediate No. II-25 disclosed in table 2 on page 101 of Japanese Unexamined Patent Publication No. 158137/1999.
(2) Preparation of Emulsifiable Concentrate
Emulsifiable concentrates were prepared by adding the test compound, acetone and Sorpol 355 (surfactant) to distilled water. These emulsions were set to contain acetone in the proportion of 5 wt. % and Sorpol 355 in the proportion of 0.01 wt. %. The concentration of the test compound was set at 20 ppm.
(3) Miticidal Test
2 ml of each emulsifiable concentrate prepared above was sprayed onto a piece of a kidney bean leaf (2×4 cm) with 30 female adults of two-spotted spider mites. After being air-dried, the leaf was placed in a thermostatic chamber having a temperature of 25±1° C. The number of live and dead mites was counted 2 days later. The mortality rate was calculated using the following equation:

Mortality rate={1−(survival rate in treated area)/(survival rate in untreated area)}×100

The use of test compound A, B or C provided a mortality rate of 100%. On the other hand, the use of test compound D provided a mortality rate of only 10%.

The results clearly show that the compounds of the present invention exhibit excellent mite control even when used at a low concentration.

TEST EXAMPLE 4 (MITICIDAL TEST ON TWO-SPOTTED SPIDER MITES)

(1) As Test Compounds, The Following Compounds Were Used:

Test compound A: Compound No. 1 in table 3 (the compound of the invention).
Test compound B: Compound No. 2 in table 3 (the compound of the invention).
Test compound C: Compound No. 10 in table 3 (the compound of the invention).
Test compound E: Compound No. a-683 disclosed in table 1-a on page 81 of Japanese Unexamined Patent Publication No. 158137/1999.

(2) Preparation of Emulsifiable Concentration

Emulsifiable concentrates were prepared by adding the test compound, acetone and Sorpol 355 (surfactant) to distilled water. These emulsions were set to contain acetone in the proportion of 5 wt. % and Sorpol 355 in the proportion of 0.01 wt. %. The concentration of the test compound was set at 200 ppm.

(3) Miticidal Test 30 ml of each emulsifiable concentrate prepared above was sprayed onto a kidney bean plant (at the stage of true leaf growth) in a 9-cm pot, and air-dried. The pot was placed in a glass greenhouse. Each of the first and second leaves was cut into a piece having a size of 3×5 cm, and 15 female adults of two-spotted spider mite were introduced thereto after 3 and 5 days of the spraying. Those pieces of leaves were placed in a thermostatic chamber having a temperature of 25±1° C. The number of live and dead mites was counted 2 days later. The mortality rate thereof was calculated in the same manner as in test example 3 above. Table 5 shows the result.

TABLE 5

| | Adjusted mortality rate (%) | |
|---|---|---|
| | 3 days after spraying | 5 days after spraying |
| Test compound A | 100 | 95 |
| Test compound B | 100 | 93 |
| Test compound C | 100 | 100 |
| Test compound E | 48 | 0 |

As shown in table 5, the compounds of the present invention exhibit excellent mite control over a long period.

TEST EXAMPLE 5 (PHYTOTOXICITY TEST)

The 20% wettable powders obtained in formulation example 2 were diluted to a predetermined degree and sprayed onto crops in a field in an amount of 0.4 liters/m$^2$. In a predetermined period after spraying, the development of phytotoxicity was observed by the naked eye. As test compounds, test compounds A, B and C above were used. Table 6 shows the result.

TABLE 6

| Crop (species) | Degree of dilution | Days after spraying | Phytotoxicity Test compound A | Test compound B | Test compound C |
|---|---|---|---|---|---|
| Orange (sour orange) | 400 | 40 | — | None | — |
| Orange (mandarin) | 1000 | 40 | — | None | — |
| Orange (iyo) | 1000 | 40 | None | None | None |
| Apple (fuji) | 1000 | 27 | None | None | None |
| Apple (jonagold) | 1000 | 14 | None | None | None |
| Tea (yabukita) | 1000 | 21 | None | None | None |
| Pear (hosui) | 2000 | 21 | None | None | None |
| Grape (pione) | 2000 | 28 | None | None | None |
| Eggplant (senryo) | 1000 | 14 | — | None | — |

Symbol "—": no test conducted.

TEST EXAMPLE 6 (PHYTOTOXICITY TEST)

As test compounds, test compounds A, B and C above were used. The 20% wettable powders prepared in formulation example 2 were diluted 500 and 1,000 times. These diluted wettable powders were sprayed onto rice plants, cucumbers, cabbages, spinaches, lettuces, tomatoes, leeks, carrots or kidney bean plants in an amount of 0.2 liters/m$^2$. The development of phytotoxicity was examined by the naked eye 7 and 14 days after the spraying. As a result, no development of phytotoxicity was observed on the plants 7 and 14 days after the spraying of the wettable powders.

Further, 20% wettable powders using test compound B were diluted 50, 100 and 200 times, and sprayed onto cucumbers, cabbages, leeks or carrots in an amount of 0.2 liters/m². The development of phytotoxicity was examined by the naked eye 7 and 14 days after spraying. As a result, no development of phytotoxicity was observed on the plants 7 and 14 days after the spraying of the wettable powders.

What is claimed is:

1. An acylacetonitrile compound represented by the formula (1):

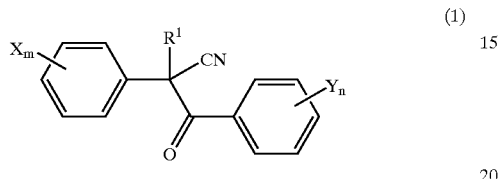

(1)

wherein $R^1$ represents —C(O)$ZR^2$; $R^2$ represents $C_{1-6}$ alkyl, $C_{1-4}$ haloalkyl, $C_{2-4}$ alkenyl, $C_{2-4}$ alkynyl, $C_{1-6}$ alkoxy-$C_{1-4}$ alkyl, $C_{1-4}$ alkylthio-$C_{1-4}$ alkyl or benzyl; Z represents oxygen or sulfur; X and Y independently represent halogen, $C_{1-6}$ alkyl or $C_{1-4}$ haloalkyl; m and n are independently an integer of 1 to 3; and m X's and n Y's may be the same or different, respectively.

2. An acylacetonitrile compound according to claim 1, wherein Z in the formula (1) represents oxygen.

3. An acylacetonitrile compound according to claim 1, wherein X in the formula (1) represents halogen or $C_{1-6}$ alkyl.

4. An acylacetonitrile compound according to claim 1, wherein Y in the formula (1) represents at least one species selected from halogen and $C_{1-4}$ haloalkyl.

5. An acylacetonitrile compound according to claim 1, wherein Z represents oxygen, X represents $C_{1-6}$ alkyl, and Y represents $C_{1-4}$ haloalkyl in the formula (1).

6. A process for preparing an acylacetonitrile compound represented by the formula (1):

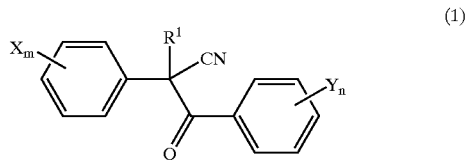

(1)

wherein $R^1$ represents —C(O)$ZR^2$; $R^2$ represents $C_{1-6}$ alkyl, $C_{1-4}$ haloalkyl, $C_{2-4}$ alkenyl, $C_{2-4}$ alkynyl, $C_{1-6}$ alkoxy-$C_{1-4}$ alkyl, $C_{1-4}$ alkylthio-$C_{1-4}$ alkyl or benzyl; Z represents oxygen or sulfur; X and Y independently represent halogen, $C_{1-6}$ alkyl or $C_{1-4}$ haloalkyl; m and n are independently an integer of 1 to 3; and m X's and n Y's may be the same or different, respectively, the process comprising reacting an α-substituted-phenylacetonitrile compound represented by the formula (2):

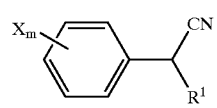

(2)

wherein $R^1$, X and m are as defined above, with a benzoyl halide represented by the formula (3):

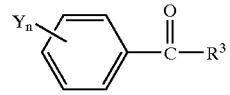

(3)

wherein Y and n are as defined above, and $R^3$ represents halogen.

7. A miticide comprising as an active ingredient an acylacetonitrile compound represented by the formula (1):

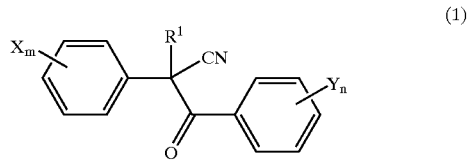

(1)

wherein $R^1$ represents —C(O)$ZR^2$; $R^2$ represents $C_{1-6}$ alkyl, $C_{1-4}$ haloalkyl, $C_{2-4}$ alkenyl, $C_{2-4}$ alkynyl, $C_{1-6}$ alkoxy-$C_{1-4}$ alkyl, $C_{1-4}$ alkylthio-$C_{1-4}$ alkyl or benzyl; Z represents oxygen or sulfur; X and Y independently represent halogen, $C_{1-6}$ alkyl or $C_{1-4}$ haloalkyl; m and n are independently an integer of 1 to 3; and m X's and n Y's may be the same or different, respectively.

8. A miticide according to claim 7, wherein Z in the formula (1) represents oxygen.

9. A miticide according to claim 7, wherein X in the formula (1) represents halogen or $C_{1-6}$ alkyl.

10. A miticide according to claim 7, wherein Y in the formula (1) represents at least one species selected from halogen and $C_{1-4}$ haloalkyl.

11. A miticide according to claim 7, wherein Z represents oxygen, X represents $C_{1-6}$ alkyl, and Y represents $C_{1-4}$ haloalkyl in the formula (1).

12. A miticide according to any of claim 7, which is effective against plant-parasitic mites.

13. A method for exterminating mites comprising applying to the site an acylacetonitrile compound represented by the formula (1):

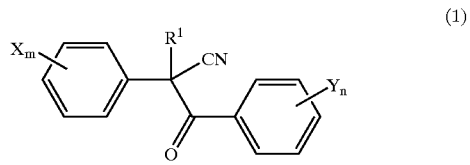

(1)

wherein $R^1$ represents —C(O)$ZR^2$; $R^2$ represents $C_{1-6}$ alkyl, $C_{1-4}$ haloalkyl, $C_{2-4}$ alkenyl, $C_{2-4}$ alkynyl, $C_{1-6}$ alkoxy-$C_{1-4}$ alkyl, $C_{1-4}$ alkylthio-$C_{1-4}$ alkyl or benzyl; Z represents oxygen or sulfur; X and Y independently represent halogen, $C_{1-6}$ alkyl or $C_{1-4}$ haloalkyl; m and n are independently an integer of 1 to 3; and m X's and n Y's may be the same or different, respectively.

14. A method for producing a miticide, said method comprising producing said miticide by using on acylacetonitrile compound represented by the formula (1):

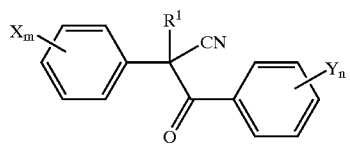

(1)

wherein $R^1$ represents —$C(O)ZR^2$; $R^2$ represents $C_{1-6}$ alkyl, $C_{1-4}$ haloalkyl, $C_{2-4}$ alkenyl, $C_{2-4}$ alkynyl, $C_{1-6}$ alkoxy-$C_{1-4}$ alkyl, $C_{1-4}$ alkylthio-$C_{1-4}$ alkyl or benzyl; Z represents oxygen or sulfur; X and Y independently represent halogen, $C_{1-6}$ alkyl or $C_{1-4}$ haloalkyl; m and n are independently an integer of 1 to 3; and m X's and n Y's may be the same or different, respectively.

15. An acylacetonitrile compound according to claim 2, wherein X in the formula (1) represents halogen or $C_{1-6}$ alkyl.

16. An acylacitonitrile compound according to claim 2, wherein Y in the formula (1) represents at least one species selected form halogen and $C_{1-4}$ haloalkyl.

17. A miticide according to claim 8, wherein X in the formula (1) represents halogen or $C_{1-6}$ alkyl.

18. A miticide according to calim 8, wherein Y in the formula (1) represents at least one species selected from halogen and $C_{1-4}$ haloalkyl.

19. Amiticide according to claim 11, which is effective against plant-parasitic mites.

* * * * *

UNITED STATES PATENT AND TRADEMARK OFFICE
CERTIFICATE OF CORRECTION

PATENT NO. : 6,899,886 B2
DATED : May 31, 2005
INVENTOR(S) : Nobuyoshi Takahashi et al.

It is certified that error appears in the above-identified patent and that said Letters Patent is hereby corrected as shown below:

Title page,
Item [56], References Cited, FOREIGN PATENT DOCUMENTS, please delete "2/1985" and insert -- 1-1985 --, therefor.

Column 24,
Line 9, please delete "calim" and insert -- claim --, therefor.
Line 12, please delete "Amiticide" and insert -- A miticide --, therefor.

Signed and Sealed this

Eighteenth Day of October, 2005

JON W. DUDAS
*Director of the United States Patent and Trademark Office*